US009192916B2

(12) United States Patent
Riley et al.

(10) Patent No.: US 9,192,916 B2
(45) Date of Patent: Nov. 24, 2015

(54) SELECTIVE HYDROGENATION OF DIENES IN THE MANUFACTURE OF MLAB

(75) Inventors: Mark G. Riley, Hinsdale, IL (US); Bryan K. Glover, Algonquin, IL (US)

(73) Assignee: UOP LLC, Des Plaines, IL (US)

( * ) Notice: Subject to any disclaimer, the term of this patent is extended or adjusted under 35 U.S.C. 154(b) by 1106 days.

(21) Appl. No.: 12/563,591

(22) Filed: Sep. 21, 2009

(65) Prior Publication Data

US 2011/0071328 A1  Mar. 24, 2011

(51) Int. Cl.
| | |
|---|---|
| C07C 5/05 | (2006.01) |
| B01J 23/58 | (2006.01) |
| B01J 21/04 | (2006.01) |
| B01J 23/44 | (2006.01) |
| B01J 35/00 | (2006.01) |
| B01J 35/10 | (2006.01) |
| C07C 5/09 | (2006.01) |
| C07C 15/107 | (2006.01) |

(52) U.S. Cl.
CPC *B01J 23/58* (2013.01); *B01J 21/04* (2013.01); *B01J 23/44* (2013.01); *B01J 35/0026* (2013.01); *B01J 35/108* (2013.01); *B01J 35/1014* (2013.01); *B01J 35/1019* (2013.01); *B01J 35/1047* (2013.01); *B01J 35/1066* (2013.01); *C07C 5/05* (2013.01); *C07C 5/09* (2013.01); *C07C 15/107* (2013.01); *C07C 2521/04* (2013.01); *C07C 2523/44* (2013.01); *C07C 2523/58* (2013.01)

(58) Field of Classification Search
CPC .......................................................... C07C 5/05
USPC ........... 585/250–277; 208/142–145; 423/713, 423/718; 502/257, 258, 260, 271, 272, 273
See application file for complete search history.

(56) References Cited

U.S. PATENT DOCUMENTS

| | | | |
|---|---|---|---|
| 4,301,316 A | 11/1981 | Young | |
| 4,301,317 A | 11/1981 | Young | |
| 4,551,443 A * | 11/1985 | Hudson | 502/313 |
| 5,574,198 A | 11/1996 | Radici et al. | |
| 6,670,516 B1 | 12/2003 | Marinangeli et al. | |
| 6,794,552 B2 | 9/2004 | Cheung et al. | |
| 7,189,885 B1 | 3/2007 | Bozzano et al. | |
| 7,288,686 B2 * | 10/2007 | Ryu | 585/259 |
| 7,294,604 B2 * | 11/2007 | Dath et al. | 502/250 |
| 7,311,815 B2 | 12/2007 | Abazajian | |
| 7,534,737 B2 | 5/2009 | Gajda | |
| 7,576,247 B2 | 8/2009 | Sohn et al. | |
| 7,683,226 B1 * | 3/2010 | Glover et al. | 585/323 |
| 2002/0107424 A1 * | 8/2002 | Cheung et al. | 585/275 |
| 2007/0032692 A1 | 2/2007 | O'Rear et al. | |
| 2007/0038007 A1 | 2/2007 | Greager et al. | |
| 2008/0248199 A1 | 10/2008 | Gajda | |
| 2009/0099399 A1 | 4/2009 | Jan et al. | |

FOREIGN PATENT DOCUMENTS

WO  WO 2004072004 A1 *  8/2004

OTHER PUBLICATIONS

U.S. Appl. No. 12/563,580, filed Sep. 21, 2009, Riley et al.
Narayanan, B.N. et al., "Alkylationof benzene with 1-octene over titania pillared montmorillonite", Reaction Kinetics and Catalysis Ltrs 94(1), 2008 p. 77-83 Kluwer Academic.
Meriaudeau, P. et al., "Zeolite based catalysts for linear alkylbenzene production: dehydrogenation of long chain alkanes", Catalysis Today, V38, N 2, p. 243-247, 1997.
Knifton, J.F. et al., A new, improved, solid-acid catalyzed process for generating linear alkylbenzenes), Catalysis Letters 75(1/2) 2001 p. 113-177.
Han, M. et al., "Synthesis of linear alkylbenzene catalyzed by HB-zeolite", Applied Catalysis A: General 238(1) 2003, p. 99-107.
Hydrocarbon Processing (ISSN 0018-8190), HPInnovations—Innovative reactor raises LAB synthesis reactor conversion, V76 N.4 40-41 (1997) Gulf Publishing Co.
Le Viness, S.C., "Polymer formation (coking), deactivation and ethylene selectivity decline", Rice Univ., 1989, 650 P, V50 N. 12 5766-B5767-B, Jun. 1990.
Murzin, D.Yu. et al., "Kinetics and stereoselectivityin gas-phase hydrogenation of alkylbenzenes over Ni/Al2O3" Reaction Kinetics and Catalysis, 71 (1) 2000 p. 47-54.
Vora, B.V. et al., "Petrochemical Developments—Latest Lab Developments", Hydrocarbon Process, V63 N. 11 86-90, Nov. 1984) Gulf Publishing Co.
Sivasanker, S et al., "Shape selective alkylation of benzene with long chain alkenes", 10th Int'l Catal Congress, Budapest, Studies in Surface Science 397-408, V75A, 1993.
Jin, Y.J. et al., "Solid acid catalyst for alkylation of benzene with long chains olefins", Petrochemical Technology 29 (10) 2000 p. 734-737.

* cited by examiner

*Primary Examiner* — In Suk Bullock
*Assistant Examiner* — Sharon Pregler

(57) ABSTRACT

A process and catalyst are presented for the selective hydrogenation of branched diolefins and acetylenes to olefins. The process uses a catalyst having large pores, and a minimal amount of micropores. The catalyst is designed to have minimal diffusional resistance through the large pores, and to minimize the hydrogenation of olefins to paraffins.

17 Claims, No Drawings

US 9,192,916 B2

SELECTIVE HYDROGENATION OF DIENES IN THE MANUFACTURE OF MLAB

FIELD OF THE INVENTION

This invention relates to economically attractive processes and a catalyst for the alkylation of aromatic compound with mono-olefin aliphatic compounds. In particular, the process and catalyst relate to the selective hydrogenation of dienes and acetylenes in the production of olefins.

BACKGROUND OF THE INVENTION

Alkylation of benzene produces alkylbenzenes that may find various commercial uses, e.g., alkylbenzenes can be sulfonated to produce detergents. In the alkylation process, benzene is reacted with an olefin the desired length to produce the sought alkylbenzene. The alkylation conditions comprise the presence of homogeneous or heterogeneous alkylation catalyst such as aluminum chloride, hydrogen fluoride, or zeolitic catalysts and elevated temperature.

More than thirty years ago, many household laundry detergents were made of branched alkylbenzene sulfonates (BABS). BABS are manufactured from a type of alkylbenzenes called branched alkylbenzenes (BAB). Alkylbenzenes (phenyl-alkanes) refers to a general category of compounds having an aliphatic alkyl group bound to a phenyl group.

The standard process used by the petrochemical industry for producing BAB consists of oligomerizing light olefins, particularly propylene, to branched olefins having 10 to 14 carbon atoms and then alkylating benzene with the branched olefins in the presence of a catalyst such as HF. The most prominent common characteristic of BAB is that, for a large proportion of BAB, there is attached to the aliphatic alkyl chain of BAB generally at least one alkyl group branch, and more commonly three or more alkyl group branches. BAB thus has a relatively large number of primary carbon atoms per aliphatic alkyl group.

Another typical characteristic of BAB is that the phenyl group in BAB can be attached to any non-primary carbon atom of the aliphatic alkyl chain. Except for 1-phenyl-alkanes whose formation is known to be disfavored due to the relative instability of the primary carbenium ion and neglecting the relatively minor effect of the branches of the branched paraffins, the oligomerization step produces a carbon-carbon double bond that is randomly distributed along the length of the aliphatic alkenyl chain, and the alkylation step nearly randomly attaches the phenyl group to a carbon along the aliphatic alkyl chain. Thus, for example, a BAB that has an aliphatic alkyl chain having 10 carbon atoms would be expected to be an approximately random distribution of 2-, 3-, 4-, and 5-phenyl-alkanes, and the selectivity to 2-phenyl alkane would be 25 if the distribution was perfectly random, but is typically between about 10 and about 40.

A third common characteristic of BAB is that one of the carbons of the aliphatic alkyl group is a quaternary carbon. The quaternary carbon may, or may not, be the carbon in the aliphatic alkyl group that is bonded by a carbon-carbon bond to a carbon in the phenyl group. When a carbon atom on the alkyl side chain not only is attached to two other carbons on the alkyl side chain and to a carbon atom of an alkyl group branch but also is attached to a carbon atom of the phenyl group, the resulting alkyl-phenyl-alkane is referred to as a "quaternary alkyl-phenyl-alkane" or simply a "quat."

It became apparent that household laundry detergents made of BABS were gradually polluting rivers and lakes. Investigation into the problem led to the recognition that BABS were slow to biodegrade. Solution of the problem led to the manufacture of detergents made of linear alkylbenzene sulfonates (LABS), which were found to biodegrade more rapidly than BABS. Today, detergents made of LABS are manufactured worldwide. LABS are manufactured from another type of alkylbenzenes called linear alkylbenzenes (LAB). LAB are phenyl-alkanes comprising a linear aliphatic alkyl group and a phenyl group and have the general formula n-phenyl-alkane. LAB has no alkyl group branches, and consequently the linear aliphatic alkyl group normally has two primary carbon atoms. Another characteristic of LAB that is produced by the standard LAB process is that the phenyl group in LAB is usually attached to any secondary carbon atom of the linear aliphatic alkyl group. In LAB produced using HF catalyst the phenyl group is slightly more likely to attach to a secondary carbon near the center as opposed to near the end of the linear aliphatic alkyl group, while in LAB produced by the Detal™ process approximately 25-35 mol-% of n-phenyl-alkanes are 2-phenyl-alkanes. U.S. Pat. Nos. 4,301,316 and 4,301,317 teach the preparation of LABs. It has also been found that lightly branched LABs, or modified LABs (MLABs), have similar or improved biodegradable characteristics as LABs.

Control over the production of MLAB is important, and the production of unbranched olefins, or monomethyl, or monoethyl olefins can improve the production of MLAB.

BRIEF SUMMARY OF THE INVENTION

The present invention is for a process of selectively hydrogenating diolefins and acetylenes in an olefin stream. The process comprises contacting the olefin stream with a large pore catalyst designed to minimize diffusional limitations, and to allow for access of normal olefins as well as for access of monomethyl and monoethyl branched diolefins into the pores. The catalyst comprises a low density support having a micropore volume of less that 10% of the total catalyst pore volume, and having a surface area less than 150 m$^2$/g.

The support comprises a material having a median pore diameter of greater than 1050 Angstroms for overcoming steric hindrances with branched diolefins, and allowing branched diolefins access to the pore interiors, to insure the diolefin composition in the pores is near the bulk diolefin composition. The support can be a gamma alumina or a theta alumina and preferably has a density of less than 0.5 g/cc and with a pore volume in the catalyst greater than 1.8 cc/g.

Other objects, advantages and applications of the present invention will become apparent to those skilled in the art from the following detailed description.

DETAILED DESCRIPTION OF THE INVENTION

The production of alkylbenzenes is important for a number of industrial uses, but mostly for the production of detergents. The production of alkylbenzenes comprises alkylating aromatic compounds using olefinic alkylating agents. The olefins can be produced from paraffins using paraffins that are only lightly branched. The source of the paraffins include paraffins generated from GTL (gas-to-liquids) processes, mono-methyl paraffins from Sorbex separation processes, and other sources of lightly branched paraffins. The use of these lightly branched paraffins are acceptable when the alkylbenzenes comprise a portion of monomethyl and/or monoethyl alkylbenzenes in the range from 1 wt. % to 70 wt. % with the remainder comprising linear alkylbenzenes.

The manufacture of MLABs from paraffins includes the step of dehydrogenating the paraffins to form linear and branched olefins. The branched olefins are lightly branched olefins and have favorable properties relative to the biodegradation of detergents manufactured from MLABs. A portion of the olefins undergo subsequent dehydrogenation and form diolefins and acetylenes. The production of high quality MLAB requires the removal of the diolefins and acetylenes. The diolefins and acetylenes are removed through a selective hydrogenation process, using a suitable catalyst for this purpose. The choice of catalyst would include a catalyst that selectively hydrogenates diolefins and acetylenes in the presence of excess olefins, has the ability to isomerizes nonconjugated diolefins into conjugated diolefins and has minimal diffusional resistance that may favor preferential removal of linear or branched diolefins.

The production of alkylbenzenes comprises passing an olefin rich stream and a feedstream comprising benzene to an alkylation reactor. The alkylation reactor has an alkylation reaction zone comprising an alkylation catalyst, and is operated at alkylation conditions to form a product stream comprising alkylbenzenes. The present invention generates an olefin rich stream comprising linear olefins and lightly branched, or modified, linear olefins to generate a product stream comprising linear alkylbenzenes and modified linear alkylbenzenes. Further details and descriptions of benzene alkylation are described in U.S. Pat. No. 7,576,247, issued Aug. 18, 2009, and which is incorporated by reference.

Selective hydrogenation catalysts used in the liquid phase often tend to suffer from diffusional limitations. These limitations can be manifest as poor selectivity, or poor olefin hydrogenation, or discrimination between linear and branched components. The production of catalyst supports often produce catalysts with bimodal pore size distributions, where pores less than 100 Angstroms in diameter are typically referred to as micropores, and pores larger than 100 Angstroms in diameter are referred to as mesopores and macropores. For purposes of this invention, the term macropores will refer to both mesopores and macropores, or to pores that have a diameter greater than 100 Angstroms. When the void fraction of the catalyst exceeds a certain fraction of the total void volume within the catalyst, a process is controlled by the micropore diffusion.

Selective hydrogenation of long chain diolefins is most commonly carried out with catalysts containing sulfided nickel on an alumina support. Sulfur can sometimes interfere with the subsequent processing of the olefins so a selective hydrogenation catalyst with good performance in the absence of sulfur is highly desirable. Since there are many selective hydrogenation units using sulfided nickel catalysts it is also desirable that the catalyst have the same operating temperature range as the catalyst it replaces. This avoids the need for additional heating or cooling of process fluids.

It is a purpose of this invention to design a catalyst that is not diffusion controlled, and that the selective hydrogenation of a mixture of diolefins in the presence of monoolefins minimizes the formation of paraffins, or minimizes the discrimination between linear and branched diolefins. The diolefins can be a mixture of linear and branched, and conjugated and non-conjugated diolefins. The mixture can also have an excess of monoolefins, such that the monoolefins are present in an amount at least ten times the amount of diolefins.

The catalyst of the present invention comprises a low density support made of gamma alumina, theta alumina or a mixture of gamma and theta alumina, and with a micropore volume of less than 20% of the total pore volume, and preferably the micropore volume is less than 10% of the total pore volume. In addition, the catalyst has a surface area of less than 150 $m^2/g$ and an active metal distributed on the support, and preferably the surface area is between 30 and 150 $m^2/g$. The active metal comprises between 50 and 5000 ppm of the catalyst by weight. The term density has several meanings, and for clarity, the term density as used herein refers to piece density. For clarity, and understanding, different density references are presented here. For true density, the density is the mass divided by its volume excluding all pores and voids. This is usually determined through x-ray or neutron diffraction analysis of single crystal samples. Apparent density, though rarely used, refers to mass divided by the volume including some portion of the pores and voids. Bulk density, or packing density, is the mass divided by the volume which includes all pores and voids or interparticle spaces. Effective solid density is determined by displacement of a give liquid, but the values obtained can vary depending upon the liquid used. Finally, the term piece density is used when the measurement is performed with a liquid which does not substantially penetrate into the pores.

A preferred embodiment for the catalyst is for the support to have a pore volume greater than 1.8 cc/g. The support is designed to have large pores, and it is preferred that the median pore diameter be greater than 1050 Angstroms. In order to overcome diffusional limitations, the large pores permit access into the pores of the diolefins, and the support is designed to have over half of the pore volume from pores having large diameters, or diameters greater than 1000 Angstroms. It is preferred that the fraction of the pore volume from the pores having diameters greater than 1000 Angstroms be greater than 60% of the total pore volume. The support is designed to have a low fraction of the micropore volume, and it is preferred to be less than 2% of the total pore volume.

In one embodiment, the preferred support is theta alumina with the theta alumina having a density of less than 0.5 g/cc. In the preparation of the support, one method is to take the support to the theta transition temperature, and convert the support to theta alumina prior to adding the active metals. In this embodiment, the active metal is palladium and is distributed on the support in an amount between 50 and 2000 ppm by weight of the catalyst, and preferably the active metal is distributed in an amount between 200 ppm and 2000 ppm, and more preferably between 200 ppm and 1000 ppm. The active metal is preferably distributed on the support using a non-chloride metal salt. One example of an alternate salt is a nitrate salt of the palladium.

The use of a catalyst in selective hydrogenation includes controlling the acidity of the catalyst. The catalyst acidity can be modified with the loading of an alkali metal onto the support. The alkali metal can be selected from group IA metals in the periodic table. Preferably, the alkali metals are selected from at least one of lithium (Li), sodium (Na), and potassium (K).

The use of the alkali metal is present in a molar concentration to the support acidity as measured by ammonia (NH3) adsorption. In the case of potassium (K), the amount of potassium is less than 3000 ppm by weight. For other metals, there is a molecular weight correction to maintain the appropriate molar concentration. For sodium the metal is in an amount less than 1800 ppm by weight, and for lithium the metal is in an amount less than 600 ppm by weight.

The development of this catalyst is for the use with lightly branched olefin feedstock containing diolefins and acetylenes. In particular, this catalyst is developed for mono-methyl and mono-ethyl branched diolefins. The lightly branched diolefins need larger pores to allow for the more sterically hindered molecules access to the pores, as well as overcoming diffusion limitations from smaller pores. Because lightly branched diolefins may react at different rates than linear diolefins, using a large pore catalyst helps insure that the concentration in the pores doesn't significantly differ from the concentration in the bulk fluid. The use of this catalyst allows for the process by having a minimization of the volume fraction of micropores, or pores having average diameters less than 100 Angstroms.

The process of the present invention is the selective hydrogenation of diolefins and acethylenes comprising contacting an olefin stream having olefins, diolefins and acetylenes with a catalyst having a micropore volume of less than 20% of the catalyst pore volume. The olefin stream contains branched diolefins and linear diolefins, with the diolefins having monomethyl and monoethyl branches. The catalyst is a low density catalyst having a low density support and a surface area of less than 150 $m^2/g$. The preferred low density support is gamma alumina or theta alumina, and the density of the support is less than 0.5 g/cc.

The catalyst includes an active metal selected from the platinum group, and the preferred metal is palladium. The active metal is deposited on the support of the catalyst in an amount between 50 and 5000 ppm by weight of the total catalyst weight, with a preferred amount of metal between 50 and 1000 ppm by weight.

The catalyst for use in the selective hydrogenation process preferably has a pore volume greater than 1.8 g/cc, and with a median pore diameter greater than 1050 Angstroms. A median pore diameter of about 1200 Angstroms is desirable. For diolefin access into the pores, the catalyst is designed to have more than half the pore volume from pores having diameters greater than 1000 Angstroms, and preferably more than 60% of the pore volume is from pores having diameters greater than 1000 Angstroms.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for the selective hydrogenation of diolefins and acetylenes, comprising:
    contacting an olefin stream comprising olefins and diolefins and acetylenes with a catalyst comprising a low density support, with the density of the support less than 0.5 g/cc, with a micropore volume of less than 10% of the catalyst pore volume and a surface area between 30 and 150 $m^2/g$, and wherein the median pore diameter of the catalyst is greater than 1050 Angstroms, wherein the low density support is gamma alumina, theta alumina or a mixture of gamma and theta alumina.

2. The process of claim 1 wherein the olefin stream comprises monomethyl and monoethyl branched diolefins and linear diolefins.

3. The process of claim 1 wherein the catalyst includes an active metal.

4. The process of claim 3 wherein the active metal is palladium.

5. The process of claim 4 wherein the palladium is in an amount between 50 and 5000 ppm by weight.

6. The process of claim 1 wherein the catalyst further comprises an alkali metal.

7. The process of claim 6 wherein the alkali metal is selected from the group consisting of lithium (Li), sodium (Na), potassium (K), and mixtures thereof.

8. The process of claim 7 wherein the alkali metal is potassium in an amount less than 3000 ppm by weight.

9. The process of claim 7 wherein the alkali metal is sodium in an amount less than 1800 ppm by weight.

10. The process of claim 7 wherein the alkali metal is lithium in an amount less than 600 ppm by weight.

11. The process of claim 5 wherein the palladium on the support is between 200 and 2000 ppm by weight.

12. The process of claim 1 wherein the pore volume in the catalyst is greater than 1.8 cc/g.

13. The process of claim 1 wherein the catalyst has more than half of the pore volume from pores having diameters greater than 1000 Angstroms.

14. The process of claim 13 wherein the catalyst has more than 60% of the pore volume from pores having diameters greater than 1000 Angstroms.

15. The process of claim 1 wherein the catalyst has a micropore volume of less than 2% of the total pore.

16. A process for the production of modified linear alkylbenzenes comprising:
    contacting an olefin stream comprising olefins and diolefins and acetylenes with a catalyst comprising a low density support, with the density of the support less than 0.5 g/cc, with a micropore volume of less than 10% of the catalyst pore volume and a surface area between 30 and 150 $m^2/g$, and wherein the median pore diameter of the catalyst is greater than 1050 Angstroms, thereby generating an olefin rich stream, wherein the low density support is gamma alumina, theta alumina or a mixture of gamma and theta alumina;
    passing the olefin rich stream and a feedstream comprising benzene to an alkylation reaction zone, operating at alkylation conditions sufficient to alkylate the benzene in the presence of an alkylation catalyst to form a product stream comprising linear alkylbenzenes and modified linear alkylbenzenes; and
    recovering the linear alkylbenzenes and modified linear alkylbenzenes from the product stream.

17. The process of claim 16 wherein the olefin stream comprises monomethyl and monoethyl branched diolefins and linear diolefins.

* * * * *